(12) United States Patent
Gaboardi et al.

(10) Patent No.: US 9,549,884 B2
(45) Date of Patent: Jan. 24, 2017

(54) RETINOID DERIVATIVES AND PROCESS FOR THEIR PREPARATION

(71) Applicant: SELEGO AB, Danderyd (SE)

(72) Inventors: Mauro Gaboardi, Novara (IT);
Graziano Castaldi, Briona (IT); Lars Fredriksson, Danderyd (SE)

(73) Assignee: SELEGO AB, Danderyd (SE)

( * ) Notice: Subject to any disclaimer, the term of this patent is extended or adjusted under 35 U.S.C. 154(b) by 0 days.

(21) Appl. No.: 14/899,121

(22) PCT Filed: Jun. 17, 2014

(86) PCT No.: PCT/SE2014/050737
§ 371 (c)(1),
(2) Date: Dec. 16, 2015

(87) PCT Pub. No.: WO2014/204390
PCT Pub. Date: Dec. 24, 2014

(65) Prior Publication Data
US 2016/0136076 A1    May 19, 2016

(30) Foreign Application Priority Data

Jun. 17, 2013  (IT) .............................. MI2013A0995

(51) Int. Cl.
*A61K 8/49*      (2006.01)
*A61Q 19/08*     (2006.01)
*C07D 213/79*    (2006.01)
*C07D 213/80*    (2006.01)
*C07D 213/82*    (2006.01)
*A61K 8/67*      (2006.01)

(52) U.S. Cl.
CPC ............. *A61K 8/4926* (2013.01); *A61K 8/671* (2013.01); *A61Q 19/08* (2013.01); *C07D 213/79* (2013.01); *C07D 213/80* (2013.01); *C07D 213/82* (2013.01); *A61K 2800/522* (2013.01); *A61K 2800/57* (2013.01); *A61K 2800/72* (2013.01)

(58) Field of Classification Search
CPC ... C07D 213/79; C07D 213/80; C07D 213/82; A61Q 19/08; A61K 8/4926; A61K 8/671; A61K 2800/522; A61K 2800/57; A61K 2800/72; A61K 2800/52
See application file for complete search history.

(56) References Cited

U.S. PATENT DOCUMENTS

| 4,055,659 A | 10/1977 | Gander et al. |
| 4,108,880 A | 8/1978 | Gander et al. |
| 4,677,120 A | 6/1987 | Parish et al. |
| 4,885,331 A | 12/1989 | Annighofer et al. |

FOREIGN PATENT DOCUMENTS

| EP | 366713 B1 | 6/1994 |
| WO | 2008/070116 A2 | 6/2008 |
| WO | 2008/154372 A1 | 12/2008 |
| WO | 2013/064681 A1 | 5/2013 |
| WO | 2013/083825 A1 | 6/2013 |

*Primary Examiner* — Sarah Pihonak
(74) *Attorney, Agent, or Firm* — Porter Wright Morris & Arthur LLP

(57) ABSTRACT

Novel retinoic acid derivatives and a process for their preparation are described.

13 Claims, 2 Drawing Sheets

Retinyl Retionate

| Date | HPLC PEAKS R.T. AND AREA PERCENTAGE ||||||||||||||
|---|---|---|---|---|---|---|---|---|---|---|---|---|---|---|
| | 12.1 | 12.2 | 13.4 | 13.8 | 14.5 | 15.1 | 16:08 | 17.9 | 20.9 | 23.0 | 25.3 | 26.1 | 26.8 |
| 23-jul | 0.42 | 0.75 | 2.72 | 0.20 | 0.52 | 0.17 | | | 0.32 | 1.88 | | 92.46 | 0.55 |
| 29-jul | 0.67 | 1.14 | 3.83 | 0.16 | 0.63 | 0.34 | | | | 1.7 | | 90.43 | 1.06 |
| 31-jul | 0.41 | 0.79 | 2.65 | 0.11 | 0.49 | 0.12 | | 0.13 | 0.54 | 1.68 | | 91.18 | 1.91 |
| 05-aug | 00:45 | 01:07 | 2.75 | 0.20 | 0.54 | 0.10 | | 0.40 | 0.69 | 1.76 | 2.31 | 90.50 | 1.52 |
| 26-aug | 00:19 | 1.94 | 2.32 | 0.036 | 0.45 | 0.079 | 0.20 | 1.13 | 2.32 | 1.31 | | 87.03 | 0.66 |

Fig. 1

| Compound (Ia) | HPLC PEAKS R.T. AND AREA PERCENTAGE | | | | | | | | | | |
|---|---|---|---|---|---|---|---|---|---|---|---|
| Date | 7.7 | 8.1 | 8.2 | 9.7 | 11.2 | 11.8 | 12.2 | 14.5 | 18.9 | 19.8 |
| 25-jun | 0.05 | 0.04 | 0.07 | 1.13 | 1.03 | 2.12 | 92.62 | 0.16 | 0.20 | 2.58 |
| 27-jun | 0.04 | 0.12 | | 1.21 | 0.92 | 2.17 | 92.57 | 0.17 | 0.27 | 2.52 |
| 01-jul | 0.06 | 0.03 | | 1.38 | 1.07 | 2.20 | 92.38 | 0.17 | 0.19 | 2.53 |
| 05-jul | | 0.12 | | 1.37 | 1.03 | 2.28 | 92.27 | 0.15 | 0.20 | 2.54 |
| 09-jul | | | | 1.06 | 0.74 | 2.93 | 92.53 | 0.14 | 0.20 | 2.38 |
| 22-jul | | | | 1.30 | 0.95 | 2.92 | 92.14 | 0.13 | 0.19 | 2.35 |
| 30-jul | | | | 1.21 | 0.99 | 2.17 | 92.53 | 0.13 | 0.45 | 2.58 |
| 26-aug | | | 0.23 | 1.91 | 0.16 | 2.38 | 92.34 | 0.13 | 0.13 | 2.00 |

Fig 2

RETINOID DERIVATIVES AND PROCESS FOR THEIR PREPARATION

FIELD OF THE INVENTION

The present invention relates to new retinoid derivatives, a process for their preparation and their uses.

BACKGROUND OF THE INVENTION

Aging is a considerable phenomenon particularly for skin where there is an increase in wrinkles, thickness, stiffness, dryness very likely also due to the exposure of the skin to the sun light for prolonged periods of time. The symptoms caused by the exposure to the sun light are defined as photo-aging and are based on changes at the level of epidermis and derma. It has been proved that photo-aging may be slackened by applying on the skin a cream containing substances such as tretinoin, retinol and derivatives thereof, alpha-hydroxy acids (AHAs).

Tretinoin is a liposoluble compound which is unstable in the living body, and is also irritant on the skin, then it could cause some side effects such as dryness, wounds and scrapings when directly applied on the skin. On the contrary, retinol can be used but, being unstable to light, heat, peroxides and oxygen, may cause additional costs for the presence of various stabilizers. Retinoids including retinol (vitamin A) and retinoic acid, isomers, derivatives and analogs thereof are well known to have beneficial effects in many skin disorders and are used in various cosmetic applications. Retinoids are also well-known to be both liable for degradation and to have a number of side-effects. For this reason there have been many attempts to stabilize retinoids both with supportive formulations and derivatization. One example is the compound retinyl retinoate (retin-15-yl ester retinoic acid (CAS No. 15498-86-9)) formed from retinoic acid and retinol with the purpose of proving a less skin irritant product with higher stability in order to find improved cosmetic use for counteracting skin aging. Other ways of stabilizing retinoids or reducing their side-effects are exemplified in European patent specifications 0366713 and 1351919; and in U.S. Pat. No. 4,677,120.

However, it remains desirable to find agents that improve the stability retinyl retinoate and being a source of retinoids will less side-effects in order to be useful for counteracting skin aging, while also being able to exert a combinatory effect useful to counteract or treat other skin disorders, both cosmetically and therapeutically. The present invention is directed to novel retinoid conjugates capable of such effects.

DESCRIPTION OF THE INVENTION

The present invention relates to compounds of formula (I)

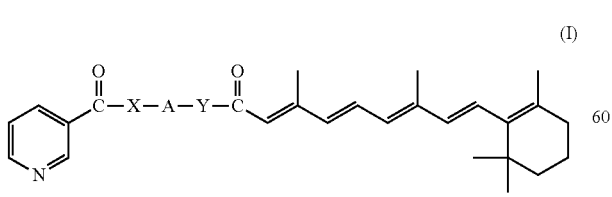

(I)

wherein
X and Y, the same or different, are NH, N-alkyl, N-aryl or an oxygen atom;

A is a linear or branched $C_{1-8}$ alkylene group (such as α,ω-alkylene); and salts thereof.

In one aspect the present invention is directed to the following compounds:

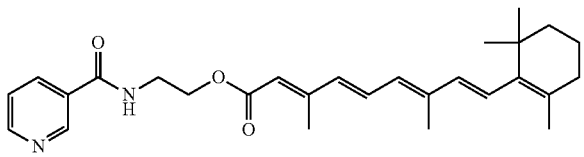

(Ia)

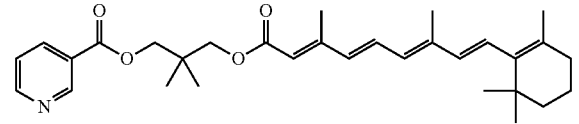

(Ib)

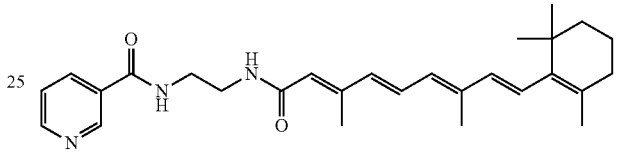

(Ic)

In one aspect of the invention relates to compounds of formula (I) compounds A, wherein X is NH; Y is an oxygen atom; and A is a linear or branched $C_{1-8}$ alkylene group.

In one aspect of the invention the compound is selected from the group consisting of 2-(nicotinamido)-ethyl retinoate, of 2-(nicotinamido)-butyl retinoate, of 5-(nicotinamido)-pentyl retinoate, and of 2-(nicotinamido)-hexyl retinoate.

The compounds of invention are useful in such applications as preventing and/or treating skin photo-aging and acne, while exerting the effects of retinoids, but exhibit an improved stability that reduces the side effects conventionally associated with retinoic acid and retinol.

In one aspect, the present invention relates to compounds according to formula (I) or as exemplified above for cosmetic use.

In one aspect, the present invention relates to compounds according to formula (I) or as exemplified above for medical use.

The compositions of the present invention are prepared according to conventional techniques and contain a suitable carrier for cosmetic or pharmaceutical use.

A further object of the present invention is a process for the synthesis of compounds of formula (I) comprising the condensation reaction of compounds of formula (II)

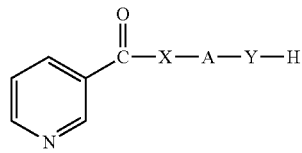

(II)

wherein A, X and Y have the above reported meanings;

with retinoic acid of formula (III)

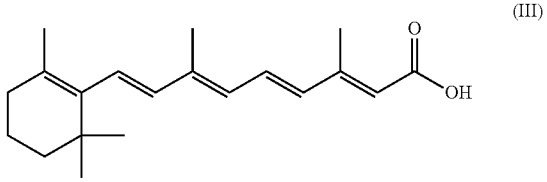 [SMILES: CC1=C(/C=C/C(C)=C/C=C/C(C)=C/C(=O)O)C(C)(C)CCC1]

(III)

in the presence of a condensing agent, optionally of a base and in an aprotic solvent to give compounds of formula (I).

The compounds of formula (II) are known and prepared according to known methods.

Suitable condensing agents for the process object of the present invention are N,N'-carbonyldiimidazole, N,N'-dicyclohexylcarbodiimide, 4,6-tri-n-propyl-2,4,6-trioxo-1,3,5,2,4,6-trioxa-triphosphorinane, preferably 4,6-tri-n-propyl-2,4,6-trioxo-1,3,5,2,4,6-trioxa-triphosphorinane is used.

The base is selected among triethylamine, diisopropylethylamine, N,N-dimethylaminopyridine, methyl nicotinate; preferably catalytic triethylamine and N,N-dimethylaminopyridine.

Suitable aprotic solvent are acetonitrile and esters; ethyl acetate is preferably used.

A preferred embodiment of the process object of the present invention is the condensation reaction of the compound of formula (IIa)

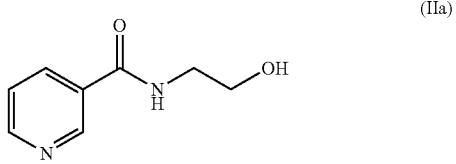 [SMILES: O=C(NCCO)c1cccnc1]

(IIa)

with retinoic acid of formula (III) in the presence of 4,6-tri-n-propyl-2,4,6-trioxo-1,3,5,2,4,6-trioxa-triphosphorinane, triethylamine and catalytic N,N-dimethylaminopyridine in ethyl acetate.

Though the invention has been described in its characteristic features, changes and equivalents which are evident to the expert in the field are included in the present invention.

The present invention will be now illustrated by some examples which are not limiting the scope of the invention.

DETAILED AND EXEMPLIFYING DESCRIPTION OF THE INVENTION

FIG. 1 and FIG. 2 show HPLC tests that represent the stability of compound (Ia) of the invention compared to retinyl retinoate.

EXAMPLE 1

Synthesis of 2-(nicotinamido)-ethyl retinoate (Ia)

In a reaction flask 0.6 g hydroxyethylnicotinamide (3.6 mmol), 5 ml ethyl acetate, 1.08 g retinoic acid (3.6 mmol), 0.8 g triethylamine (7.92 mmol), catalytic N,N-dimethylaminopyridine were charged and under stirring, at about 25° C., 2.52 g of a 50% solution of 4,6-tri-n-propyl-2,4,6-trioxo-1,3,5,2,4,6-trioxa-triphosphorinane in ethyl acetate (3.96 mmol) was added. The reaction mixture was kept under these conditions for fifteen hours and when the reaction was complete 5 ml of water were added. The organic phase was washed with sodium hydroxide 1N (1×5 ml) and hydrochloric acid 1N (1×5 ml). The organic phase was brought to residue by distillation under vacuum, and purified by column chromatography (eluent: methylene chloride:methanol 97.5:2.5), to give 1 g of 2-(nicotinamido)-ethyl retinoate as a solid. $^1$H-NMR (CDCl$_3$, 300 MHz): δ 8.99 (d, 1H), 8.68 (dd, 1H), 8.11 (dt, 1H), 7.35 (dd, 1H), 7.10 (m, 1H), 7.00 (dd, 1H), 6.25 (m, 2H), 6.16 (m, 2H), 5.75 (s, 1H), 4.33 (t, 2H), 3.75 (m, 2H), 2.32 (s, 3H), 1.99 (m, 4H), 1.68 (s, 3H), 1.50 (m, 3H), 1.43 (m, 2H), 0.98 (s, 6H).

EXAMPLE 2

Synthesis of 2,2-dimethylpropyl-retinyl nicotinate (Ib)

In a reaction flask 0.6 g 3-hydroxy-2,2-dimethylpropyl-nicotinate (3.6 mmol), 5 ml ethyl acetate, 1.08 g retinoic acid (3.6 mmol), 0.8 g triethylamine (7.92 mmol), catalytic N,N-dimethylaminopyridine were charged and under stirring, at about 25° C., 2.52 g of a 50% solution of 4,6-tri-n-propyl-2,4,6-trioxo-1,3,5,2,4,6-trioxa-triphosphorinane in ethyl acetate (3.96 mmol) was added. The reaction mixture was kept under these conditions for fifteen hours and when the reaction was complete 5 ml of water were added. The organic phase was washed with sodium hydroxide 1N (1×5 ml) and hydrochloric acid 1N (1×5 ml). The organic phase was brought to residue by distillation under vacuum, and purified by column chromatography (eluent:methylene chloride:methanol 97.5:2.5), to give 1 g of 2,2-dimethylpropyl-retinyl nicotinate as a solid. $^1$H-NMR (CDCl$_3$, 300 MHz): δ 8.99 (d, 1H), 8.68 (dd, 1H), 8.11 (dt, 1H), 7.35 (dd, 1H), 7.10 (m, 1H), 7.00 (dd, 1H), 6.25 (m, 2H), 6.16 (m, 2H), 5.75 (s, 1H), 4.17 (t, 2H), 4.07 (m, 2H), 2.32 (s, 3H), 1.99 (m, 4H), 1.82 (s, 3H), 1.74 (m, 2H), 1.68 (s, 3H), 1.50 (m, 3H), 1.43 (m, 2H), 0.98 (s, 6H).

EXAMPLE 3

Synthesis of 2-(aminoethyl)-retinyl nicotinate (Ic)

In a reaction flask 0.6 g 2-aminoethyl-nicotinamide (3.6 mmol), 5 ml ethyl acetate, 1.08 g retinoic acid (3.6 mmol), 0.8 g triethylamine (7.92 mmol), catalytic N,N-dimethylaminopyridine were charged and under stirring, at about 25° C., 2.52 g of a 50% solution of 4,6-tri-n-propyl-2,4,6-trioxo-1,3,5,2,4,6-trioxa-triphosphorinane in ethyl acetate (3.96 mmol) was added. The reaction mixture was kept under these conditions for fifteen hours and when the reaction was complete 5 ml of water were added. The organic phase was washed with sodium hydroxide 1N (1×5 ml) and hydrochloric acid 1N (1×5 ml). The organic phase was brought to residue by distillation under vacuum, and purified by column chromatography (eluent: methylene chloride:methanol 97.5:2.5), to give 1 g of 2-(aminoethyl)-retinyl nicotinate as a solid. $^1$H-NMR (CDCl$_3$, 300 MHz): δ 8.99 (d, 1H), 8.89 (d, 1H), 8.68 (dd, 1H), 8.11 (dt, 1H), 7.35 (dd, 1H), 7.10 (m, 1H), 7.00 (dd, 1H), 6.25 (m, 2H), 6.16 (m, 2H), 5.75 (s, 1H), 4.33 (t, 2H), 3.75 (m, 2H), 2.32 (s, 3H), 1.99 (m, 4H), 1.68 (s, 3H), 1.50 (m, 3H), 1.43 (m, 2H), 0.98 (s, 6H).

EXAMPLE 4

Synthesis of N-(5-hydroxypentyl)nicotinamide

In a reaction flask 1.00 g nicotinic acid (8.12 mmol), 5 ml dichloromethane, were charged and under stirring, at about 0-5° C., 1.13 g of oxalyl chloride were added and when the reaction was complete 10 ml of dichloromethane were added. When the reaction was complete, the solvent and the oxalyl chloride where removed by distillation under vacuum to give 1.4 g of nicotinoyl chloride. In a reaction flask 5 ml dichloromethane, 0.29 g 5-aminopentanol (2.8 mmol), 0.623 g trietilamine (6.16 mmol) were charged and under stirring, at about −10° C., 0.5 g of nicotinoyl chloride were added. The reaction mixture was kept at 25° C. for one hour and when the reaction was complete 5 ml of water were added. The aqueous phase was extracted with methyl-tetrahydrofuran (2×5 ml) and the organic phase was brought to residue by distillation under vacuum to give 0.4 g of N-(5-hydroxypentyl)nicotinamide.

EXAMPLE 5

Synthesis of 5-(nicotinamido)-pentyl retinoate

In a reaction flask 0.4 g N-(5-hydroxypentyl)nicotinamide (1.91 mmol), 5 ml acetonitrile, 0.56 g imidazoyl-retinoate (1.60 mmol), 0.026 g 1,5,7-triazabicyclo[4.4.0]dec-5-ene (0.19 mmol) were charged. The reaction mixture was kept at 25° C. for two hours and when the reaction was complete 5 ml of water were added. The organic phase was washed with hydrochloric acid 1N (1×5 ml) and the aqueous phase was basified until pH 9 with sodium hydroxide 1N and extracted with ethyl acetate (2×5 ml). The organic phase was brought to residue by distillation under vacuum, to give 0.9 g of 5-(nicotinamido)-pentyl retinoate.
$^1$H-NMR (CDCl3, 300 MHz): δ 8.95 (s, 1H), 8.61 (m, 1H), 8.10 (m, 1H), 7.29 (m, 1H), 7.16 (m, 1H), 6.90 (m, 1H), 6.23 (m, 2H), 6.14 (m, 2H), 5.67 (s, 1H), 4.04 (m, 2H), 3.41 (m, 2H), 2.26 (s, 3H), 1.94 (m, 3H), 1.65 (s, 3H), 1, 60 (m, 4H), 1.44 (m, 4H), 0.97 (s, 6H).

EXAMPLE 6

Synthesis of N-(1-hydroxybutan-2-yl)nicotinamide

In a reaction flask 5.00 g methyl-nicotinate (36.46 mmol), 25 ml acetonitrile, 0.51 g 1,5,7-triazabicyclo[4.4.0]dec-5-ene (3.65 mmol), 3.25 g 2-amino-1-butanol (36.46 mmol) were charged. The reaction mixture was kept under the reflux temperature for two hours and when the reaction was complete the temperature was brought to 25° C. and the solvent was removed by distillation under vacuum to give 7.5 g of N-(1-hydroxybutan-2-yl)nicotinamide crude.

EXAMPLE 7

Synthesis of 2-(nicotinamido)-butyl retinoate

In a reaction flask 3.83 g N-(1-hydroxybutan-2-yl)nicotinamide crude (0.020 mol), 5.26 g imidazoyl-retinoate (0.015 mol), 0.5 g 1,5,7-triazabicyclo[4.4.0]dec-5-ene (0.00359 mol), 50 ml ethyl acetate were charged. The reaction mixture was kept at 25° C. overnight and when the reaction was complete 20 ml of water were added. The organic phase was washed with water (1×14 ml), aqueous sodium bicarbonate (1×14 ml), water (1×14 ml) and sodium chloride (2×14 ml). The organic phase was brought to residue by distillation under vacuum, the solid formed was filtrated and washed with water, then with hexane and was dried in a vacuum oven to give 5.9 g of 2-(nicotinamido)-butyl retinoate. $^1$H-NMR (CDCl3, 300 MHz): δ 8.95 (m, 1H), 8.63 (m, 1H), 8.07 (m, 1H), 7.32 (m, 1H), 6.91 (m, 1H), 6.23 (m, 2H), 6.08 (m, 2H), 5.72 (s, 1H), 4.31 (m, 2H), 4.19 (m, 1H), 2.29 (s, 3H), 1.98 (m, 6H), 1.66 (s, 3H), 1, 57 (m, 4H), 1.43 (m, 2H), 0.97 (m, 8H). Melting point: 114-115° C.

EXAMPLE 8

Synthesis di N-(6-hydroxyhexyl)nicotinamide

In a reaction flask 10 ml dichloromethane, 0.476 g 5-amino-1-esanol (4.06 mmol), 0.82 g triethylamine (8.12 mmol) were charged and under stirring, at about −10° C., 0.72 g of nicotinoyl chloride (4.06 mmol, obtained according to Example 4) were added. The reaction mixture was kept at 25° C. for one hour and when the reaction was complete 5 ml of water were added. The aqueous phase was extracted with methyl-tetrahydrofuran (2×5 ml) and the organic phase was brought to residue by distillation under vacuum to give 0.5 g N-(6-hydroxyhexyl)nicotinamide.

EXAMPLE 9

Synthesis di 6-(nicotinamido)-hexyl retinoate

In a reaction flask 0.5 g N-(6-hydroxyhexyl)nicotinamide (2.5 mmol), 0.796 g imidazoyl-retinoate (2.27 mmol), 0.031 g 1,5,7-triazabicyclo[4.4.0]dec-5-ene (0.227 mmol), 5 ml ethyl acetate were charged. The reaction mixture was kept at 25° C. for two hours and when the reaction was complete 5 ml of water were added and the organic phase was washed with hydrochloric acid 1N. The aqueous phase was basified until pH 9 with sodium hydroxide 1N and extracted with ethyl acetate (2×5 ml). The organic phase was washed with sodium chloride saturated solution (1×5 ml) and brought to residue by distillation under vacuum, to give 1 g of 6-(nicotinamido)-hexyl retinoate. $^1$H-NMR (CDCl3, 300 MHz): δ 9.03 (m, 1H), 8.70 (m, 1H), 8.17 (m, 1H), 7.41 (m, 1H), 6.98 (m, 1H), 6.55 (m, 1H), 6.26 (m, 2H), 6.12 (m, 2H), 5.75 (s, 1H), 4.10 (m, 2H), 3.45 (m, 2H), 2.32 (s, 3H), 2.01 (m, 5H), 1.70 (s, 3H), 1, 62 (m, 6H), 1.43 (m, 6H), 1.00 (s, 6H). Melting point: 102-105° C.

EXAMPLE 10

A comparison in stability between Compound (Ia) and the substance retin-15-yl ester retinoic acid (CAS No. 15498-86-9) was outlined by performing HPCL analysis of the two compounds throughout an extended storage period.

The stability study was performed at 0-4° C. and 40-90% humidity. The samples of each product, packed in polyethylene bag inside a closed polyethylene box, were maintained under the above mentioned condition for the given time (see below). The stability of the product was checked by HPLC analysis using the method reported here below: A Young Lin YL9100 HPLC System was equipped with a variable volume automatic injector and a YL-Clarity data system. A Capcellpack UG 120 C-18, 150×4.6 mm, 5 μm, column from Agilent Technologies was used with a column temperature of 25±2° C., a flow rate of 1.5 ml/min, an injection volume of 10 μl, a wavelength of 326 nm. The mobile phase was A: water containing 0.1% acetic acid; B: acetonitrile containing 0.1% acetic acid; C: methanol containing 0.1% acetic acid; and D: isopropanol. For a run time of 40 min the gradient was:

TABLE 1

| Time (min) | Phase A (%) | Phase B (%) | Phase C (%) | Phase D (%) |
|---|---|---|---|---|
| 0 | 32 | 8 | 60 | 0 |
| 1 | 32 | 8 | 60 | 0 |
| 10 | 2 | 38 | 60 | 0 |
| 11 | 2 | 38 | 60 | 0 |
| 22 | 2 | 48 | 25 | 25 |
| 28 | 2 | 48 | 25 | 25 |
| 29 | 2 | 58 | 0 | 40 |
| 31 | 2 | 58 | 0 | 40 |
| 32 | 32 | 8 | 60 | 0 |
| 40 | 32 | 8 | 60 | 0 |

The Working Solution: dissolve the sample under stability study in acetonitrile in a concentration of 1 mg/ml and inject as it.

With reference to FIG. 1 and FIG. 2, the HPLC peaks with the highest area percentage (retention time 26.1 for Compound (1a) and 12.2 for retin-15-yl ester retinoic acid). Accordingly, the stability data show that after about two months Compound (Ia) is practically stable, whereas the purity of for retin-15-yl ester retinoic acid (retinyl retinoate) decreases in one month by 5% lower with respect to the starting time.

EXAMPLE 11

In Vitro Skin Corrosion Membrane Barrier Test

The skin corrosive potential of compound (1a) was analyzed. Corrosive chemicals are dependent on their grade of corrosivity able to break through the bio-barrier membrane employed in the "in vitro Membrane barrier test (CORROSITEX® Assay)" (see EVCAM (2000) ESAC statement on the application of the Corrositex® assay for skin corrosivity testing. The test system is composed of a synthetic bio-barrier that is placed on a chemical detection system (CDS). The time necessary to activate the CDS allows to distinguish between Corrosive© and non-corrosive (NC) test substances. Hereby the test item was placed atop the bio-barrier membranes. The CDS activation was assessed as a color change or a change in consistency. In the present study the test substance including compound (1a) showed no corrosive effects as mean time required to activate the CDS was >60 min. Compound (1a) accordingly was classified as non-corrosive.

EXAMPLE 12

In-Vitro Cytotoxicity Test

The cytotoxic effects of compound (1a) were analyzed using the uptake of the vital dye neutral red as measure of cytotoxicity. The assay was performed using BALB/c 3T3 cells. Prior to the assay a growth curve was performed to confirm the appropriate doubling time and identity of the cells. Cell doubling time was determined to 22.2 h. The highest soluble concentration compound (1a) was found to be 2 mg/ml in DMSO resulting in a highest concentration of 10 micrograms/ml in a dose range finding experiment.

In the dose range finding experiment, the test item showed no cytotoxicity exceeding the 50%-level up to the highest concentration (10 micrograms/ml). Therefor no IC50 could be calculated and no LD50 value could be determined. Additionally, no main test using adjusted concentrations near the range finder IC50 could be performed.

In this study under the given conditions the starting for rodent acute oral systemic toxicity studies could not be predicted since no adequate cytotoxicity for the calculation of an IC50 value could be generated due to limited solubility of compound (1a).

EXAMPLE 13

In Vitro Skin Irritation Test

The skin irritant potential of compound (1a) was analyzed with a reconstituted three-dimensional human epidermis model, the EPISKIN-Standard Model® (EPISKIN-SM®) as a replacement for the Draize Skin Irritation Test (OECD TG 404) to distinguish between UN GHS "Category 2" skin irritating test substances and not categorized test substances ("No Category") which may be considered as non-irritant. Hereby, the test item was applied topically. Cytotoxicity is expressed as reduction of mitochondrial dehydrogenase activity measured by formazan production from MTT after a 15 min exposure and 42 h post incubation period and compared to those of the concurrent negative controls.

In the conditions of the study, compound (1a) showed no irritant effects. The relative mean tissue viability after 15 min of exposure and 42 h post incubation was >50%. The test item, compound (1a) is therefore classified as "non-irritant" in accordance with UN GHS "No Category".

EXAMPLE 14

In Vitro Phototoxicity Test

In the present study the phototoxicity effects of compound (1a) were analyzed by dissolving the test item in DMSO and diluting to 1.100 ratio with Earle's balanced test solution. BALB/C 3T3 cells were treated for 1 h with different concentrations of the test solution at 37±1±° C. and further 50 min in absence and in presence of a non-toxic dose of UVA light, respectively. One day after treatment cytotoxicity was analyzed as a measure of reduction of neutral red uptake and compared to the controls. In this study, under given conditions, the test item showed a slight cytotoxic effect in case of UVA radiation. However, since the calculated mean photo effect (MPE) is <0.1 (0.027 in a rangefinder experiment; 0.056 in the main experiment) the test item is classified as non-toxic.

EXAMPLE 15

In Silico Predictions

In silico data for the Compound (1a) and the substance retin-15-yl ester retinoic acid (CAS No. 15498-86-9) were used for a dermal sensitization potential assessment.

The predictions of the toxicological and physicochemical properties were evaluated in terms of the reliability as required by OECD principles of validation for regulatory purposes of (Quantitave Structure Activity Relationship (QASR) Models ((http://www.oecd.org/document/23/0, 2340,en2649_34365_33957015_1_1_1_1,00.html).

Two prediction models with different approaches were used in order to apply a consensus approach in order to improve the reliability. The prediction models used were the Vega QSAR model and the Toxtree decision rule system. Skin sensitization was estimated by Toxtree decision rule system, which identifies alerts for skin sensitization using a SMARTS pattern based approach (Enoch S J, Madden J C, Cronin M T. SAR&QSAR Environ Res. 2008, 19(5-6), 555-78).

Toxtree identified potential structural alert for skin sensitization, leading to the conclusion that the substance is SKIN SENSITIZER.

The Vega model for skin sensitization produces as output two values positive and negative that represents the belonging degree respectively to the sensitizer and non-sensitizer classes.

Vega predicted substance as SKIN SENSITIZER, but the result is not reliable since the two structures are out of the applicability domain.

The skin sensitization was predicted employing two different in silico approaches: the decision rule system provided by Toxtree and the QSAR model as provided by Vega. The two approaches were employed in order to apply a consensus analysis to enhance the reliability of the prediction. Only reliable predictions were taken into account in the consensus assessment, therefore, in this case, the consensus prediction was based on Toxtree results, leading to the conclusion that the substance is SKIN SENSITIZER.

The result, however, is moderately reliable. Table 2, below illustrates the results of the Vega and Toxtree prediction of skin senzitation.

TABLE 2

| In silico tool | Compound (1a) | Reliability assessment | retin-15-yl ester retinoic acid | Reliability assessment |
|---|---|---|---|---|
| Toxtree | SKIN SENSITIZER | — | SKIN SENSITIZER | — |
| Vega | SKIN SENSITIZER | NOT RELIABLE | SKIN SENSITIZER | NOT RELIABLE |
| CONSENSUS | SKIN SENSITIZER | | SKIN SENSITIZER | |

This study was designed to generate estimated in silico (non-testing) data for −1 and the similar substance retin-15-yl ester retinoic acid to be used for its dermal sensitization potential assessment. Table 3 below provides a summary of the in silico predictions computed and discussed in details in the paragraphs above.

TABLE 3

| Endpoint: dermal sensitization | Overall result | Note |
|---|---|---|
| Compound (1a) | SENSITIZING | The in silico prediction should be confirmed by experimental testing |
| retin-15-yl ester retinoic acid | SENSITIZING | |

It should be considered that the little reliable predictions of Vega could be complemented by the potential reactivity domains identified by Toxtree, leading to reasonable skin sensitization predictions. However, if an experimental result shows no sensitization potential, this negative result could be taken into account for the risk assessment.

The invention claimed is:

1. A compound of formula (I)

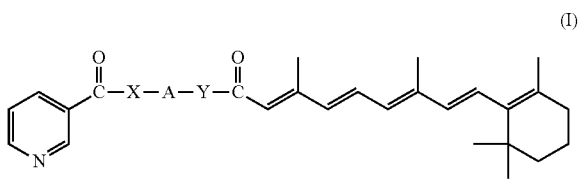

wherein,
X and Y are the same or different and are NH, N-alkyl, N-aryl or an oxygen atom;
A is a linear or branched $C_{1-8}$ alkylene group;
or a salt thereof.

2. A compound according to claim 1 selected from a group of compounds of consisting of formula (1a), (1b) and (1c):

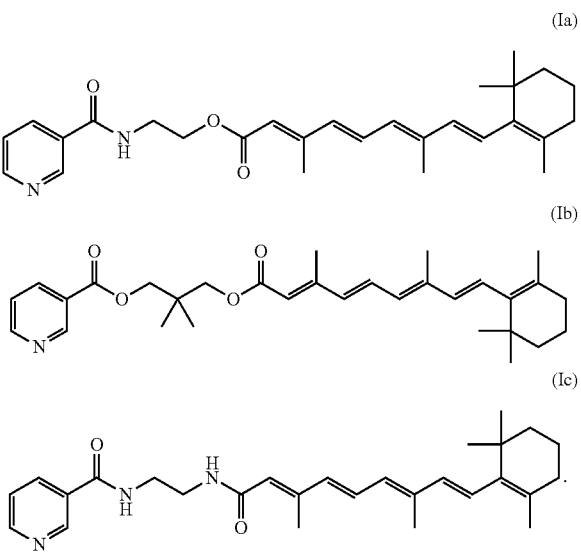

3. A compound according to claim 1, wherein
X is NH;
Y is an oxygen atom; and
A is a linear or branched $C_{1-8}$ alkylene group.

4. A compound according to claim 3, selected from the group consisting of 2-(nicotinamido)-ethyl retinoate, of 2-(nicotinamido)-butyl retinoate, of 5-(nicotinamido)-pentyl retinoate, and of 2-(nicotinamido)-hexyl retinoate.

5. A process for the preparation of a compound according to claim 1 comprising the condensation reaction of a compound of formula (II)

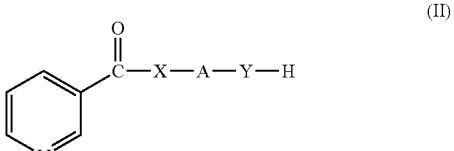

wherein A, X and Y have the meanings as defined in claim 1;

with retinoic acid of formula (III)

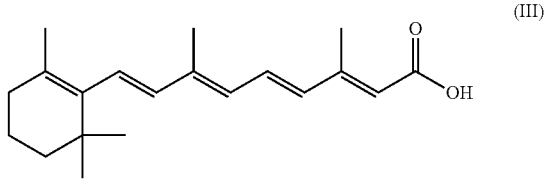 [SMILES: CC1=C(/C=C/C(C)=C/C=C/C(C)=C/C(=O)O)C(C)(C)CCC1]

in the presence of a condensing agent, optionally of a base and in an aprotic solvent.

6. A process according to claim 5, wherein the condensing agent is selected among N,N'-carbonyldiimidazole, N,N'-dicyclohexylcarbodiimmide, and 4,6-tri-n-propyl-2,4,6-trioxo-1,3,5,2,4,6-trioxa-triphosphorinane.

7. A process according to claim 5, wherein the base is selected among triethylamine, diisopropylethylamine, N,N-dimethylaminopyridine, and methyl nicotinate.

8. A process according to claim 5, wherein the aprotic solvent is selected among acetonitrile and esters.

9. A cosmetic composition comprising a compound according to claim 1 and a cosmetically acceptable carrier.

10. A pharmaceutical composition comprising a compound according to claim 1 and a pharmaceutically acceptable carrier.

11. A process according to claim 5, wherein the condensing agent is 4,6-tri-n-propyl-2,4,6-trioxo-1,3,5,2,4,6-trioxa-triphosphorinane.

12. A process according to claim 5, wherein the base is selected among triethylamine and catalytic N,N-dimethylaminopyridine.

13. A process according to claim 5, wherein the aprotic solvent is ethyl acetate.

* * * * *